United States Patent [19]

Hart et al.

[11] Patent Number: 5,342,848
[45] Date of Patent: Aug. 30, 1994

[54] THIOFORMAMIDE DERIVATIVES

[75] Inventors: Terance W. Hart; Bernard Y. J. Vacher, both of Dagenham, United Kingdom

[73] Assignee: Rhone-Poulenc Rorer Limited, Eastbourne, England

[21] Appl. No.: 917,025

[22] PCT Filed: Feb. 8, 1991

[86] PCT No.: PCT/EP91/00247

§ 371 Date: Aug. 7, 1992

§ 102(e) Date: Aug. 7, 1992

[87] PCT Pub. No.: WO91/12242

PCT Pub. Date: Aug. 22, 1991

[30] Foreign Application Priority Data

Feb. 8, 1990 [GB] United Kingdom ............... 9002879

[51] Int. Cl.$^5$ ............... C07D 213/16; C07D 213/18; C07D 401/02; A61K 31/44
[52] U.S. Cl. ............... 514/357; 514/332; 514/335; 514/336; 514/351; 546/256; 546/261; 546/263; 546/268; 546/283; 546/284; 546/300; 546/331
[58] Field of Search ............... 546/261, 263, 268, 276, 546/283, 284, 300, 331, 256; 514/332, 336, 351, 357, 335

[56] References Cited

U.S. PATENT DOCUMENTS 5,246,950 9/1993 Hart ............... 514/357

FOREIGN PATENT DOCUMENTS 0321274 6/1987 European Pat. Off. .
0377532 7/1990 European Pat. Off. .
0390693 10/1990 European Pat. Off. .
1351024 4/1974 United Kingdom .

OTHER PUBLICATIONS

Winslow et al., European Journal of Pharmacology, 131 (1986) pp. 219–228.
Karaki, H., J. Pharmacol. Methods, 18 (1987) pp. 1–21.

*Primary Examiner*—Marianne M. Cintins
*Assistant Examiner*—Phyllis G. Spivack
*Attorney, Agent, or Firm*—James A. Nicholson; Martin F. Savitzky; Raymond S. Parker, III

[57] ABSTRACT

Thioformamide derivatives of formula (I):

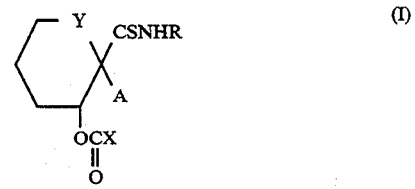

wherein R represents alkyl; A represents optionally substituted pyrid-4-yl; Y represents ethylene or methylene or a direct bond and X represents an optionally substituted phenyl, pyridyl, furyl or thienyl group or optionally substituted alkyl, alkenyl or cycloalkyl, and salts thereof possessing useful pharmacological properties.

7 Claims, No Drawings

THIOFORMAMIDE DERIVATIVES

This invention relates to new therapeutically useful thioformamide derivatives, to processes for their preparation and to pharmaceutical compositions containing them.

The new thioformamide derivatives of the present invention are those compounds of formula (I), hereinafter depicted wherein:

R represents an alkyl group;

A represents a heteroaromatic group selected from pyrid-4-yl and quinolin-4-yl, optionally substituted by an alkyl or alkoxy group, or a halogen atom;

Y represents: an ethylene or methylene group or a direct bond; and

X represents either:
- a) a phenyl, pyridyl, furyl or thienyl group, each of which may be optionally substituted by one or more substituents selected from halogen atoms; hydroxy, alkyl, $C_{2-4}$-alkenyl, alkoxy, phenoxy, tetrahydropyranyloxy, alkanoyl, benzoyl, cyano, nitro, trifluoromethyl, carboxy, amino, (optionally hydroxy)alkylamino, di(optionally hydroxy)alkylamino, trialkylammonio, alkoxycarbonylamino, alkanoylamino, benzoylamino, alkanoyloxy and alkoxycarbonyl groups, and carbamoyl groups (unsubstituted or substituted by one or two alkyl groups in turn optionally substituted by hydroxy groups, or by a straight- or branched-chain divalent group containing from 4 to 6 atoms in the chain and which may contain a further heteroatom so as to form, for example, piperazinocarbonyl or piperidinocarbonyl groups); or
- b) a straight- or branched-chain alkyl group (containing from 1 to 6 carbon atoms), alkenyl group (containing from 2 to 6 carbon atoms) or cycloalkyl group (containing from 3 to 6 ring carbon atoms), each of which may be optionally substituted by one or more substituents selected from halogen atoms; phenyl, naphthyl, imidazolyl and pyridyl groups (each optionally substituted as defined for phenyl, pyridyl, furyl or thienyl groups in a) above); hydroxy, $C_{2-4}$-alkenyl, alkoxy, phenoxy, tetrahydropyranyloxy, alkanoyl, benzoyl, cyano, nitro, carboxy, amino, (optionally hydroxy)alkylamino, di(optionally hydroxy)alkylamino, trialkylammonio, alkoxycarbonylamino, alkanoylamino, benzoylamino, alkanoyloxy and alkoxycarbonyl groups; and carbamoyl groups (unsubstituted or substituted by one or two alkyl groups in turn optionally substituted by hydroxy groups, or by a straight- or branched-chain divalent group containing from 4 to 6 atoms in the chain and which may contain a further heteroatom so as to form, for example, piperazinocarbonyl or piperidinocarbonyl groups);

wherein all alkyl groups and moieties can be straight-chain or branched, and, unless otherwise specified, contain one to four carbon atoms;
and pharmaceutically acceptable salts thereof.

Particularly important classes of compounds of formula (I) exhibit one of more of the following features:
i) R represents a methyl group;
ii) A represents a pyrid-4-yl group, preferably unsubstituted;
iii) Y represents a methylene group; and
iv) X represents a phenyl group, preferably unsubstituted;

the other symbols being as hereinbefore defined, and their pharmaceutically acceptable salts.

The presence of a carbonyloxy group on the ring creates an isomeric center in the molecule which in association with the adjacent asymmetric ring carbon atom leads to 4 stereoisomers which, optionally, can be separated into 2 racemic pairs. The racemic pair and enantiomers in which the —OCOX and —CSNHR groups are in the trans relationship are preferred.

In certain cases the substituents A, X, and R can also contribute to stereoisomerism. All such forms are also embraced by the present invention.

A particularly important compound of the present invention is:

A. (±)-trans-2-benzoyloxy-N-methyl-1-(pyrid-4-yl)cyclohexanecarbothioamide as well as its stereoisomeric forms and pharmaceutically acceptable salts thereof.

The letter A is allocated to the compound for ease of reference in other parts of the specification.

The compounds have valuable pharmacological properties, in particular properties which are indicative of utility in the treatment and/or prophylaxis of disorders associated with:

(1) vascular smooth muscle contraction including hypertension and other cardiovascular disorders such as congestive heart failure, and conditions associated with tissue ischaemia such as angina, peripheral vascular disease and cerebrovascular disease;

(2) respiratory smooth muscle contraction including reversible airways obstruction and asthma;

(3) contraction of smooth muscle of gastrointestinal tract, urinary bladder and uterus, including peptic ulcers, irritable bowel syndrome and diverticular disease; and premature labor.

The compounds also have utility in the inhibition of head hair loss associated with male pattern baldness, by topical application.

Compounds within the scope of the present invention exhibit positive pharmacological activities as demonstrated by tests which are believed to correlate to pharmacological activity in humans and other animals.

For example, compounds of general formula (I) were submitted to:

Vaso-relaxant Activity Tests

The test methods used were adapted from those described by Winslow et al [Eur. J. Pharmacol., 131, 219–228 (1986)] and Karaki [J. Pharmacol. Methods, 18, 1–21 (1987)] for differentiating vaso-relaxant activity.

Test A: Activity Against Contractions Induced by Low $K^+$ Concentrations in the Isolated Rat Aorta Thoracic aorta was removed from rats and transverse strips, denuded of endothelium, were suspended in a bath containing Krebs solution. The tension was recorded and a contraction induced by addition of 20 mM $K^+$ (potassium ion) to the bathing solution. The test compound was added to the bath as a solution in increasing cumulative concentration. The concentration in the bathing solution of the compound A which reduced the $K^+$-induced contraction by 90% was determined, and expressed as the effective concentration ($EC_{90}$), was 0,003 $\mu$M.

The compounds of general formula (I) can be prepared by the application and adaptation of known methods, for example as hereinafter identified. By the term "known methods" as used in this specification is meant methods heretofore used or described in the literature.

According to a feature of the present invention, the compounds of general formula (I), as hereinbefore defined, are prepared by the reaction of a compound of general formula (II), wherein A, Y and R are as hereinbefore defined, with a carboxylic acid of general formula

XCOOH         (III)

or an acid halide, preferably chloride, or reactive acid anhydride thereof, wherein X is as hereinbefore defined. The reaction with a carboxylic acid is generally carried out in an inert, organic solvent, optionally in the presence of a proton acceptor and of a coupling agent, such as dicyclohexylcarbodiimide or carbonyldiimidazole.

Reaction with an acid halide is also generally carried out in an inert solvent, optionally in the presence of a proton acceptor.

Reaction with an anhydride is carried out under similar conditions to that with an acid halide.

Compounds of formula (III) may be generated in situ from salts thereof.

Typical solvents include acetonitrile, pyridine, dichloromethane, chloroform, acetone, dimethylformamide, water and mixtures thereof.

Typical proton acceptors may be organic bases such as triethylamine or, preferably, 4-dimethylaminopyridine or inorganic bases such as sodium bicarbonate.

Reaction temperatures for all three reaction variations typically vary from $-30°$ C. to reflux.

The compounds of general formula (II), wherein A, Y and R are as hereinbefore defined, may be prepared by the reduction of the corresponding compounds of general formula (IV).

The reduction can be carried out in an inert organic solvent such as methanol or dimethylsulphoxide, or a mixture of these solvents at a temperature from $-20°$ C. to $+50°$ C., using an alkali metal borohydride, e.g. sodium borohydride.

Alternatively the reduction can be carried out using an aluminum alkoxide (e.g. the isopropoxide) in an alcoholic solvent (e.g. isopropanol) at temperatures up to reflux.

Both reactions produce both the cis and trans compounds.

Compounds of general formula (IV), wherein A, Y and R are as hereinbefore defined may be prepared by the reaction of a compound of general formula (V), wherein A and Y are as hereinbefore defined, with an isothiocyanate of the general formula:

R—N=C=S         (VI)

wherein R is as hereinbefore defined. The reaction is generally carried out in an anhydrous inert organic solvent such as tetrahydrofuran, dimethylformamide or hexamethylphosphoramide, or a mixture of these solvents, at a temperature from $-80°$ C. to $+50°$ C., in the presence of an inorganic base such as potassium tert.-butoxide, or an organo-lithium derivative such as n-butyllithium, or of sodium hydride.

A stereoselective synthesis of the compounds of formula (IV) may be carried out by reaction of a mixture of enantiomers of general formula (V) with a chiral auxiliary agent, before being reacted with a compound of general formula (VI) as hereinbefore described followed by the removal of the chiral auxiliary agent.

The chiral auxiliary agent is typically a compound of formula:

Q—NH$_2$         (VII)

wherein Q is a chiral group, for example asymmetrically substituted pyrrolidino. Preferred pyrrolidines include 1-amino-2-methoxymethyl pyrrolidine.

Reaction of a compound of formula (V) with a compound of formula (VII) produces a compound of formula (VIII). Reaction of this with a compound of formula (VI) preferentially produces one enantiomer of compound of formula (IX). The chiral compound of formula (IV) can be produced therefrom by hydrolysis.

Compounds of formula (V), wherein A is as hereinbefore defined and Y is a methylene or ethylene group, can be made via a dehydrobromination/rearrangement reaction of compounds of formula (X), wherein A is as defined above and $Y^1$ is methylene or ethylene. This may be initiated by a bromide extracting agent such as a silver salt (e.g. silver perchlorate) and carried out in an inert anhydrous solvent (for example an ether such as tetrahydrofuran).

Compounds of formula (X), wherein A and $Y^1$ are as defined above, can be made by the addition of hypobromous acid across the double bond of compounds of formula (XI), wherein A and $Y^1$ are as defined above. This may be done by reaction with a brominating agent (e.g. 1,3-dibromo-5,5-dimethylhydantoin) in an aqueous acidic medium, optionally in the presence of a cosolvent.

Compounds of formula (XI), wherein A and y1 are as defined above, can be made via a coupling reaction between a phosphorane of formula (XII) (typically made in situ by the reaction of a compound of formula (XIII), wherein $Y^1$ is as defined above and $R^1$ and Z are conventional groups present in a Wittig reagent and its phosphonium salt precursor [e.g. phenyl and bromine respectively], with a strong base, such as potassium t-butoxide, in an anhydrous solvent, such as tetrahydrofuran, preferably under an inert atmosphere) and a compound of formula:

A—CHO         (XIV)

wherein A is as defined above.

Alternatively compounds of formula (V), wherein Y is ethylene, methylene or a direct bond and A is as hereinbefore defined, can be made by the removal of methanol from compounds of formula (XV), wherein A. and Y are as defined above. This is typically carried out in the presence of a strongly acidic agent (e.g. phosphorus pentoxide or sulphuric acid), optionally in a solvent (such as toluene) and at elevated temperature, followed by hydrolysis of the intermediate enol ether.

Compounds of formula (XV) can be made by reaction of a compound of formula:

A—$Z^1$         (XVI)

wherein A is as defined above and $Z^1$ is a halogen, preferably bromine or chlorine, atom, in the presence of a strong base, such as an alkyl lithium (e.g. butyllithium), with a compound of formula (XVII), wherein Y is as defined above, in an inert solvent such as an ether (e.g. diethyl ether) or a hydrocarbon (e.g. toluene).

Alternatively, compounds of general formula (IV), wherein A and Y are as hereinbefore defined and R is methyl, can be prepared from compounds of general formula (XVIII), wherein A and Y are as defined above and $R^2$ is an alkyl group of 1 to 4 carbon atoms or a benzyl or carboxymethyl group, by reaction with methylamine. The reaction is generally carried out with an excess of amine, without a solvent or in an inert organic solvent such as an ether (e.g tetrahydrofuran), an aromatic hydrocarbon or an alcohol, or a mixture of these solvents, at a temperature from room temperature to 130° C., optionally under pressure. The amine may be added in an alcoholic (preferably ethanolic) solution.

It may be advantageous for the thiol formed during the reaction to be fixed in the form of a heavy metal salt using a thiol acceptor such as mercuric chloride.

Compounds of formula (XVIII), wherein Y, A and $R^2$ are as hereinbefore defined, may be prepared by the reaction of compounds of formula (V), wherein Y and A are as hereinbefore defined, with carbon disulphide followed by reaction with a compound of formula:

$$R^2-Z^2 \quad (XIX)$$

wherein $R^2$ is as hereinbefore defined and $Z^2$ is a halogen, preferably chlorine, bromine or iodine, atom or a readily displaceable ester group such as methanesulphonyloxy or 4-toluenesulphonyloxy. The reaction is generally carried out in an anhydrous inert organic solvent such as tetrahydrofuran, to which hexamethylphosphoramide may be added, at a temperature from −80° C. to +50° C. in the presence of an organic base such as potassium tert.-butoxide, or an organo-lithium derivative such as butyllithium, or sodium hydride.

The starting materials and the intermediates, such as compounds of formulae (III), (VI), (VII), (XIII), (XIV), (XVI), (XVII) and (XIX), can be made by application or adaptation of known methods or are readily available.

It Will be understood that it may be desirable to change one or more of the substituents on the alkyl or aryl groups at an appropriate stage during the synthesis of the compounds of the invention. For example, the compounds of general formula (I) wherein A represents a phenyl group substituted by a carbamoyl group may be alternatively prepared from the corresponding compounds-of general formula (I) wherein A represents a phenyl group substituted by a cyano group by the application or adaptation of known methods for such conversion.

It is to be understood that the conversion, for example by known methods, of one compound of general formula (I) into another compound of formula (I) constitutes a feature of the present invention.

By the term "pharmaceutically acceptable salts" as used in this specification is meant salts the anions or cations of which are relatively innocuous to the animal organism when used in therapeutic doses so that the beneficial pharmaceutical properties of the parent compounds of general formula (I) capable of forming salts are not vitiated by side-effects ascribable to those anions or cations.

It is to be understood that, where in this specification reference is made to compounds of formula (I), it is intended to refer also, where the context so permits, to their pharmaceutically acceptable salts.

Suitable acid addition salts for use in pharmaceuticals may by selected from salts derived from inorganic acids, for example hydrochlorides, hydrobromides, phosphates, sulphates and nitrates, and organic acids, for example oxalates, lactates, tartrates, acetates, salicylates, citrates, propionates, succinates, fumarates, maleates, methylene-bis-$\beta$-hydroxynaphthoates, gentisates and di-p-toluoyltartrates.

Suitable salts with bases include alkali metal (e.g. sodium and potassium), alkaline earth metal (e.g. calcium and magnesium), ammonium and amine (e.g. diethanolamine, triethanolamine, octylamine, morpholine and dioctylmethylamine) salts.

As well as being useful in themselves as active compounds, salts of the compounds of general formula (I) capable of forming salts with acids or bases are useful for the purposes of purification of the parent compounds of general formula (I), for example by exploitation of the solubility differences between the salts and the parent compounds, by techniques well known to those skilled in the art.

The compounds obtained by the above processes can be purified by the usual physical methods, in particular crystallization and chromatography, especially to resolve mixtures of enantiomers using a chiral column.

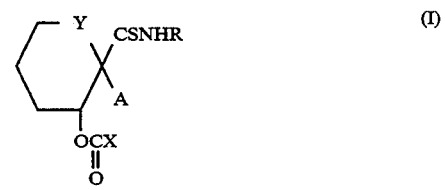

(I)

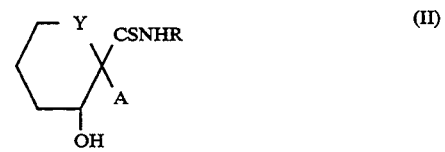

(II)

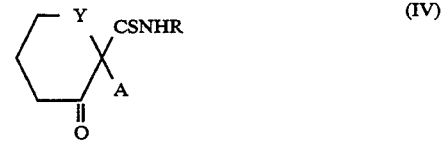

(IV)

(V)

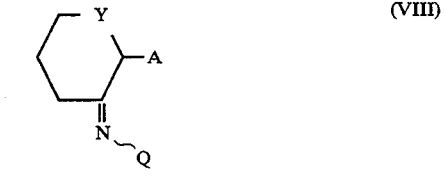

(VIII)

(IX)

-continued

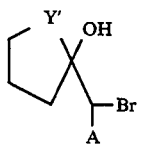 (X)

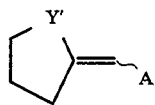 (XI)

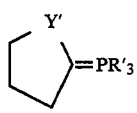 (XII)

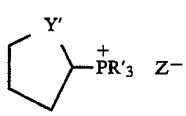 (XIII)

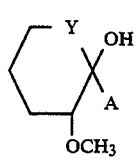 (XV)

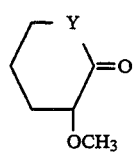 (XVII)

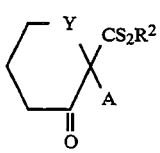 (XVIII)

The following Example illustrates the preparation of compounds according to the present invention

EXAMPLE 1

Compound A

4-Dimethylaminopyridine (360mg, 2.9mmol) was added to a stirred suspension of (+)-trans-N-methyl-2-hydroxy-1-(pyrid-4-yl) cyclohexanecarbothioamide (0.65g, 2.6retool) in a mixture of pyridine (2.5ml) and dichloromethane (7.5ml) and the mixture stirred for 15 minutes. Benzoyl chloride (0.46g, 3.3mmol) was added and the reaction mixture stirred at room temperature for 21 hours. This was concentrated in vacuo and the residue was dissolved in dichloromethane (40 ml) and the solution washed with water (25ml), saturated aqueous sodium bicarbonate solution (25ml) and brine (25 ml), dried (MgSO$_4$) and evaporated in vacuo to produce a foam which was triturated with diethyl ether and recrystallized from acetonitrile to give (+)-trans-2-benzoyloxy-N-methyl-1-(pyrid-4-yl)cyclohexanecarbothioamide, a white solid, (0.49 g, 1.4retool), m.p. 186.5°–188.5° C.;

Found: C, 67.7; H, 6.2; N, 7.9; S, 9.0%. Calculated for C$_{20}$H$_{22}$N$_2$O$_2$S: C, 67.8; H, 6.3; N, 7.9; S, 9.0%.

REFERENCE EXAMPLE 1

A mixture of (±)-N-methyl-2-oxo-1-(pyrid-4-yl)cyclohexanecarbothioamide (0.54 g, 2.2 mmol) and aluminum isopropoxide (0.89 g, 4.4 mmol) in dry isopropanol (50 ml) was refluxed at 120° C. for 1 hour under a McIntyre head. The reaction mixture was then cooled and concentrated in vacuo. The residue was dissolved in chloroform (50 ml) which was then extracted with aqueous sodium potassium tartrate solution (50 ml). The aqueous layer was back-extracted with chloroform (50 ml) and the combined organic extracts were washed with tartrate solution (25 ml) and brine (25 ml), dried (MgSO$_4$) and concentrated in vacuo. The residue was recrystallized from acetonitrile to give (±)-trans-2-hydroxy-N-methyl-1-(pyrid-4-yl)cyclohexanecarbothioamide (0.58 g, 2.3mmol), m.p. 151°–153° C.

The reaction also produced the cis isomer which could be isolated from the reaction mixture.

REFERENCE EXAMPLE 2

A vigorously stirred solution of (+)-2-(pyrid4-yl)cyclohexanone (2.47 g, 14.1mmol) in anhydrous dimethylformamide (40ml) was cooled to −40° C. and potassium t-butoxide (1.74 g, 15.5 mmol) was added in one portion. The reaction mixture was stirred for 10 minutes, allowed to warm to room temperature, stirred for a further 30 minutes and then cooled to −40° C.

Methyl isothiocyanate (1.24g, 16.9 mmol) was added in one portion and the reaction mixture was stirred at −40° C. for 5 minutes, allowed to warm to room temperature, left standing overnight and then poured into water (200 ml). The mixture was adjusted to pH 4 with acetic acid and extracted with ethyl acetate (3×75 ml). The combined organic extracts were washed with saturated aqueous sodium bicarbonate solution (50 ml) and brine (50 ml), dried (MgSO$_4$) and evaporated in vacuo. The residue was washed with diethyl ether and recrystallized from ethyl acetate in the presence of charcoal to give (±)-N-methyl-2-oxo-1-(pyrid-4-yl)-cyclohexanecarbothioamide (1.0 g, 4mmol), m.p. 182°–183° C.

Found: C, 62.9; H, 6.3; N, 11.2; S, 12.9%. Calculated for C$_{13}$H$_{16}$N$_2$OS: C, 62.9; H, 6.5; N, 11.3; S, 12.9%.

REFERENCE EXAMPLE 3

(±)-cis/trans-2-Methoxy-1-(pyrid-4-yl)cyclohexanol (25.7 g, 0.12 mmol) was added portionwise to stirred, ice-cooled, concentrated sulphuric acid (185 ml) such that the temperature was maintained at 10°–15° C. After addition was complete the mixture was allowed to warm to room temperature and the stirring continued until 1.5 hours had elapsed from starting the addition.

The reaction mixture was poured into an ice/water mixture (1.51) and stirred for 10 minutes. The mixture was then partially neutralized by the addition, with cooling, of a solution of sodium hydroxide (277g) in water (400ml), the temperature being kept below 25° C. Sodium carbonate was then added until pH8 was reached and the filtered precipitate was washed with ethyl acetate. The aqueous phase was saturated with sodium chloride and extracted with ethyl acetate (2×500 ml). The combined ethyl acetate solutions were dried (MgSO$_4$) and concentrated in vacuo to give a red oil which, on seeding and trituration with diethyl ether gave (±)-2-(pyrid-4-yl)-cyclohexanone (5.76 g, 35mmol), m.p. 99°–101° C.

REFERENCE EXAMPLE 4

A stirred solution of 2.5M n-butyllithium in hexane (30.8ml, 0.77mol) at −78° C. was mixed with diethyl ether (310ml) and a solution of 4-bromopyridine (60.9g, 0.39mol) in diethyl ether (1200 ml) was added dropwise over 3 hours. Stirring was continued for 2 hours and a solution of 2-methoxycyclohexanone (54.3g, 0.42mol) in diethyl ether (total volume 100ml) was added dropwise over 1 hour. The stirred solution was allowed to warm to room temperature and stirring was continued overnight. Water (250ml) was then added to the reaction mixture, keeping the temperature below 20° C. and the mixture stirred for a further 30 minutes. The organic layer was separated and the aqueous layer was extracted with diethyl ether (3×50ml). The combined organic layers were extracted with hydrochloric acid (2N, 2×250ml+100ml) and the combined acidic extracts brought to pH 11 with 5N aqueous sodium hydroxide and extracted with ethyl acetate (3×250ml). The combined ethyl acetate extracts were dried (MgSO$_4$) and evaporated in vacuo. The residue was recrystallized from petroleum ether (60°–80° C.) to give (±)-2-methoxy-1-(pyrid-4-yl)cyclohexanol (32.0g, 0.15mol) as a mixture of cis and trans isomers, m.p. 98°–101° C.

The present invention includes within its scope pharmaceutical compositions which comprise a compound of general formula (I) or a pharmaceutically acceptable salt thereof, in association with a pharmaceutically acceptable carrier or coating. In clinical practice the compounds of the present invention may be administered rectally, but are preferably administered parenterally, by inhalation if appropriate, or, more preferably, orally.

Solid compositions for oral administration include compressed tablets, pills, powders and granules. In such solid compositions, one or more of the active compounds is, or are, admixed with at least one inert diluent such as starch, sucrose or lactose.

The compositions may also comprise, as is normal practice, additional substances other than inert diluents, e.g. lubricating agents, such as magnesium stearate.

Liquid compositions for oral administration include pharmaceutically acceptable emulsions, solutions, suspensions, syrups and elixirs containing inert diluents commonly used in the art such as water and liquid paraffin. Besides inert diluents such compositions may comprise adjuvants, such as wetting, and suspending agents, and sweetening, flavoring, perfuming and preserving agents. The compositions according to the invention for oral administration also include capsules of absorbable material such as gelatin, containing one or more of the active substances with or without the addition of diluents or excipients.

Compositions according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. The compositions may also contain adjuvants such as stabilizing, preserving, wetting, emulsifying and dispersing agents. They may be sterilized by, for example, filtration through a bacteria-retaining filter, by incorporation in the compositions of sterilizing agents, by irradiation or by heating. They may also be manufactured in the form of sterile solid compositions, which can be dissolved in sterile water or some other sterile injectable medium immediately before use.

Compositions for inhalation may be sterile aqueous solutions which are then nebulized or dry powders formulated in accordance with known methods.

Solid compositions for rectal administration include suppositories formulated in accordance with known methods and containing one or more of the compounds of formula (I) or a pharmaceutically acceptable salt thereof.

The percentage of active ingredient in the composition of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration, the duration of the treatment and the condition of the patient. In the adult, the doses are generally from about 0.001 to about 50, preferably from about 0.01 to about 5, mg/kg body weight per day by oral administration. By inhalation, either as a nebulized solution or as a formulated dry powder, the preferred daily dosage is from about 0.001 to about 5, preferably from about 0.01 to about 0.5, mg/kg body weight.

The compounds may also be applied topically for inhibition of head hair loss associated with male pattern baldness, the preferred daily dosage being from about 0.1 to about 10 mg/kg body weight applied, for example, in 5ml portions two or three times per day.

The following Example illustrates pharmaceutical compositions according to the present invention.

COMPOSITION EXAMPLE

No. 2 size gelatin capsules each containing:

| | |
|---|---|
| (±)-trans-2-benzoyloxy-N-methyl-1-(pyrid-4-yl)-cyclohexanecarbothioamide | 20 mg |
| lactose | 100 mg |
| starch | 60 mg |
| dextrin | 40 mg |
| magnesium stearate | 1 mg | were prepared in accordance with the usual procedure.

We claim:

1. A compound of the formula

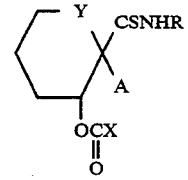

wherein
R is alkyl;
A is pyrid-4-yl or pyrid-4-yl substituted by alkyl, alkoxy or halogen;
Y is ethylene, methylene or a bond;
X is:
  a) phenyl, pyridyl, furyl or thienyl, each of which may be substituted by one or more substituents selected from halogen, hydroxy, straight- or branched-chain $C_{1-4}$alkyl, $C_{2-4}$alkenyl, $C_{1-4}$alkoxy, phenoxy, tetrahydropyranyloxy, alkanoyl, benzoyl, cyano, nitro, trifluoromethyl, carboxy, amino, $C_{1-4}$alkylamino, hydroxy $C_{1-4}$alkylamino, di-$C_{1-4}$alkylamino, di-$C_{1-4}$alkylamino substituted by hydroxy, tri-$C_{1-4}$alkylammonio, $C_{1-4}$alkoxycarbonyl, alkanoylamino, benzoylamino, alkanoyloxy, $C_{1-4}$alkoxycarbonyl, carbamoyl, mono- or di-$C_{1-4}$alkylcarbamoyl, mono- and di-$C_{1-4}$alkylcarbamoyl substituted by hydroxy or by straight- or branched-chain divalent groups of about 4 to about 6 carbon atoms in the chain which may further contain a hetero atom; or b) straight- or branched-chain alkyl of 1 to about 6 carbon atoms, alkenyl of 2 to about 6 carbon atoms or cycloalkyl of 3 to about 6 carbon atoms, each of which may be substituted by one or more substituents selected from halogen, hydroxy, $C_{2-4}$-alkenyl, $C_{1-4}$alkoxy, phenoxy, tetrahydropyranyloxy, alkanoyl, benzoyl, cyano, nitro, carboxy, amino, $C_{1-4}$alkylamino, hydroxy $C_{1-4}$alkylamino, di-$C_{1-4}$alkylamino, di-$C_{1-4}$alkylamino substituted by hydroxy, tri-$C_{1-4}$alkylammonio, $C_{1-4}$alkoxycarbonylamino, alkanoylamino, benzoylamino, alkanoyloxy, $C_{1-4}$alkoxycarbonyl, carbamoyl, mono- or di-$C_{1-4}$alkylcarbamoyl, mono- and di-$C_{1-4}$alkylcarbamoyl substituted by hydroxy or by straight- or branched-chain divalent groups of about 4 to about 6 carbon atoms in the chain which may further contain a hetero atom, phenyl, naphthyl, imidazolyl, pyridyl or substituted phenyl, naphthyl, imidazolyl and pyridyl where said substituents are selected from halogen, hydroxy, $C_{1-4}$alkyl, $C_{2-4}$alkenyl, $C_{1-4}$alkoxy, phenoxy, tetrahydropyranyloxy, alkanoyl, benzoyl, cyano, nitro, trifluoromethyl, carboxy, amino, $C_{1-4}$alkylamino, hydroxy $C_{1-4}$alkylamino, di-$C_{1-4}$alkylamino, di-$C_{1-4}$alkylamino substituted by hydroxy, tri-$C_{1-4}$alkylammonio, $C_{1-4}$alkoxycarbonylamino, alkanoylamino, benzoylamino, alkanoyloxy, $C_{1-4}$alkoxycarbonyl, carbamoyl, mono- or di-$C_{1-4}$alkylcarbamoyl, mono and di-$C_{1-4}$alkylcarbamoyl substituted by hydroxy or by straight- or branched-chain divalent groups of about 4 to about 6 carbon atoms in the chain which may further contain a hetero atom; and pharmaceutically acceptable salts thereof.

2. A compound according to claim 1 wherein:
R is methyl;
Y is methylene; and
X is substituted or unsubstituted phenyl.

3. A compound according to claim 2 wherein the pyrid-4-yl group is unsubstituted and the phenyl group is unsubstituted.

4. A pharmaceutical composition for use in the treatment of a patient having a disorder in need of vaso-relaxant activity which comprises a therapeutically effective amount of a compound of claim 1 in an amount effective to relax vascular smooth muscle in association with a pharmaceutically acceptable carrier or diluent.

5. A method for the treatment of a patient having a disorder in need of vaso-relaxant activity which comprises administering to the patient a compound of claim 1 in an amount effective to produce relaxation of vascular sooth muscle.

6. A compound according to claim 1, wherein the —OCOX and —CSNHR groups are trans to each other.

7. A compound according to claim 1, (±)-trans-2-benzoyloxy-N-methyl-1-(pyrid-4-yl)cyclohexanecarbothioamide, stereoisomers and pharmaceutically acceptable salts thereof.

* * * * *